United States Patent
Walker et al.

(10) Patent No.: US 7,149,562 B2
(45) Date of Patent: Dec. 12, 2006

(54) NEEDLE WITH FIBEROPTIC CAPABILITY

(75) Inventors: Steven C. Walker, Waxahachie, TX (US); John M. Shepherd, San Antonio, TX (US); Leopoldo C. Cancio, San Antonio, TX (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 245 days.

(21) Appl. No.: 10/663,684

(22) Filed: Sep. 17, 2003

(65) Prior Publication Data

US 2004/0127776 A1    Jul. 1, 2004

Related U.S. Application Data

(60) Provisional application No. 60/411,050, filed on Sep. 17, 2002.

(51) Int. Cl.
  *A61B 5/00* (2006.01)
(52) U.S. Cl. .................. 600/339; 600/341; 600/342
(58) Field of Classification Search ........ 600/309–310, 600/323, 325, 327, 341–342; 606/13–16; 607/88
  See application file for complete search history.

(56) References Cited

U.S. PATENT DOCUMENTS

| | | | |
|---|---|---|---|
| 3,941,121 A | 3/1976 | Olinger et al. | |
| 4,281,645 A * | 8/1981 | Jobsis | 600/324 |
| 5,436,454 A * | 7/1995 | Bornstein et al. | 250/339.12 |
| 5,460,182 A * | 10/1995 | Goodman et al. | 600/342 |
| 5,551,424 A * | 9/1996 | Morrison et al. | 600/342 |
| 5,987,346 A | 11/1999 | Benaron et al. | |
| 6,280,703 B1 * | 8/2001 | Combs et al. | 424/9.1 |
| 6,285,896 B1 * | 9/2001 | Tobler et al. | 600/338 |
| 6,298,253 B1 * | 10/2001 | Buschmann | 600/342 |
| 6,584,335 B1 * | 6/2003 | Haar et al. | 600/322 |
| 6,594,518 B1 * | 7/2003 | Benaron et al. | 600/342 |
| 6,746,404 B1 * | 6/2004 | Schwartz | 600/486 |
| 2002/0107448 A1 | 8/2002 | Gandjbakche et al. | |
| 2003/0216663 A1 | 11/2003 | Jersey-Willuhn et al. | |

* cited by examiner

*Primary Examiner*—Eric F. Winakur
(74) *Attorney, Agent, or Firm*—Elizabeth Arwine

(57) ABSTRACT

A needle with fiber optic capability for spectrophotometric analysis includes a needle assembly including a needle body having an open tip and side radiation ports. A fiber optic element is disposed in the needle assembly for carrying electromagnetic radiation to the open tip area for transmission to a target area. Fiber optic bundles in communication with the radiation ports are disposed in the needle body for transmitting backscattered radiation to a light detector or sensor for spectrophotometric analysis. The needle assembly may include barbs for anchoring the device in place.

23 Claims, 4 Drawing Sheets

NEEDLE WITH FIBEROPTIC CAPABILITY

This application claims the benefit of priority under 35 U.S.C. § 119(e) to U.S. Ser. No. 60/411,050 filed on Sep. 17, 2002.

I. FIELD OF THE INVENTION

The present invention relates to diagnostic and monitoring devices. More particularly, the present invention relates to diagnostic and monitoring devices having fiber optic capabilities.

II. BACKGROUND OF THE INVENTION

Devices for monitoring, measuring, or diagnosing a physiological condition or a biological phenomenon are known in the art. Some of these devices are able to quickly and/or non-invasively evaluate a condition or detect a phenomenon by using spectrophotometry. For example, a number of procedures for monitoring or diagnosing medical conditions benefit from the ability to use spectrometric means to accomplish the procedure. An example is pulse oximetry. As will be appreciated by one of ordinary skill in the art, the degree of oxygen saturation of hemoglobin, $SpO_2$, in arterial blood is often a vital index of the condition of a patient. As blood is pulsed through the lungs by action of the heart, a certain percentage of the deoxyhemoglobin, Hb, oxygenates so as to become oxyhemoglobin, $HbO_2$. From the lungs, the blood passes through the arterial system until it reaches the capillaries at which point a portion of the $HbO_2$ delivers its oxygen to support the life processes in adjacent cells.

By medical definition, the oxygen saturation level is the ratio of $HbO_2$ to the total hemoglobin; therefore as will be appreciated, $SPO_2=HbO_2/(Hb+HbO_2)$. The saturation value is a significant physiological value. A healthy, conscious person will have an oxygen saturation of approximately 96 to 98%. A person can lose consciousness or suffer permanent brain damage if that person's oxygen saturation value falls to very low levels for an extended period of time. Because of the importance of the oxygen saturation value, pulse oximetry has been recommended as a standard of care for every general anesthetic.

As stated, some pulse oximeters use spectrophotometry to determine the saturation value of blood. Specifically, these oximeters analyze the change in color of the blood to determine the saturation value. As will be appreciated, when radiant energy passes through a liquid and/or tissue, certain wavelengths may be selectively absorbed by particles which are dissolved therein. For a given path length that the light traverses through the liquid, Beer's law (the Beer-Lambert or Bouguer-Beer relation) indicates that the relative reduction in radiation power (P/Po) at a given wavelength is an inverse logarithmic function of the concentration of the solute in the liquid that absorbs that wavelength.

For a solution of oxygenated human hemoglobin, the absorption maximum is at a wavelength of about 640 nanometers (red), therefore, instruments that measure absorption at this wavelength are capable of delivering clinically useful information concerning oxyhemoglobin levels.

In general, methods for non-invasively measuring oxygen saturation in arterial blood utilize the relative difference between the electromagnetic radiation absorption coefficient of deoxyhemoglobin, Hb, and that of oxyhemoglobin, $HbO_2$.

It is well known that deoxyhemoglobin molecules absorb more red light than oxyhemoglobin molecules, and that absorption of infrared electromagnetic radiation is not affected by the presence of oxygen in the hemoglobin molecules. Thus, both Hb and $HbO_2$ absorb electromagnetic radiation having a wavelength in the infrared (IR) region to approximately the same degree; however, in the visible region, the light absorption coefficient for Hb is quite different from the light absorption coefficient of $HbO_2$ because $HbO_2$ absorbs significantly more light in the visible spectrum than Hb.

In the practice of the typical "pulse oximetry" technique, the oxygen saturation of hemoglobin in intravascular blood is determined by (1) alternatively illuminating a volume of intravascular blood with electromagnetic radiation of two or more selected wavelengths, e.g., a red wavelength and an infrared wavelength, (2) detecting the time-varying electromagnetic radiation intensity transmitted through or reflected by the intravascular blood for each of the wavelengths, and (3) calculating oxygen saturation values for the patient's blood by applying the Lambert-Beer's transmittance law to the detected transmitted or reflected electromagnetic radiation intensities at the selected wavelengths.

As will be appreciated from the foregoing, whereas apparatuses are available for making accurate measurements on a sample of blood in a cuvette (in vitro), these devices suffer from the drawback that they do not permit in vivo, in situ, analysis. As it is not always possible or desirable to withdraw blood from a patient, and it obviously is impractical to do so when continuous monitoring is required, such as while the patient is in surgery. Therefore, much effort has been expended in devising instrumentation for making such measurements by noninvasive or less invasive means.

The pulse oximeters used today are desk-top models or handheld models that are interfaced to the patient through the use of a multi-wire bundle. Despite their seemingly manageable size and the sophistication of technology, these units are still bound by several limitations. For example, as will be appreciated by one of ordinary skill in the art, these devices are still too big and unwieldy for use in monitoring smaller vessels and areas of circulation. Also, as will be appreciated, these prior art devices lack the minute size and ability to be coupled to a particular area of a patient for continuous monitoring of a precise area or condition in, for example, a trauma situation.

The foregoing and like drawbacks are also limiting on other monitoring and diagnosing devices and methods. For example, presently, hand-held Doppler ultrasound is used to monitor surgical flap integrity. As will be appreciated, ultrasound is useful only in monitoring larger arteries and is ill adapted to give information about the circulation at the capillary bed level. Likewise, surgical flaps and grafts often have tenuous blood supplies which make it very difficult to monitor them effectively with the currently available devices.

Moreover, the use of spectrophotometric monitoring of deep tissues and organs for oxygenation, indocyanine green clearance and other like spectrophotometric phenomenon is, at best, difficult and cumbersome with the currently available devices.

The foregoing underscores some of the problems associated with conventional diagnosing and monitoring devices. Furthermore, the foregoing highlights the long-felt, yet unresolved need in the art for a portable and reliable device adapted to allow a user to monitor a particular area of interest, even if at the capillary bed level or even if having a tenuous blood supply, with isolated or continuous spectrophotometric means.

III. SUMMARY OF THE INVENTION

The present invention overcomes the practical problems described above and offers new advantages as well. One object of the invention is to provide a diagnosing and monitoring device. According to this object of the invention, one aspect of the invention is to provide a diagnosing and monitoring device adapted to allow spectrophotometric analysis of deep tissues and organs for oxygenation, indocyanine green clearance and other phenomenon. In accordance with another aspect of the invention there is provided a diagnosing and monitoring device adapted for monitoring surgical flaps and grafts despite tenuous blood supplies or the need for remote positioning of the device in a patient's body. According to yet another aspect of the invention there is provided a diagnosing and monitoring device adapted to allow continuous monitoring of a vital condition of a patient or a tissue, in for example, a trauma situation.

In accordance with these aspects of the invention, in one embodiment of the invention there is provided a medical device comprising a needle assembly. In accordance with this embodiment, the needle assembly has a needle body having a lumen extending therethrough. The lumen may have fiber optic bundles in the form of threads or cables disposed within the lumen of the body. Furthermore, the body preferably defines a plurality of ports. The ports preferably are adapted for the fiber optics to carry electromagnetic radiation, such as light and/or infrared radiation, to and from an area to be monitored or diagnosed in the vicinity of the needle body. In a presently preferred embodiment, there are multiple side ports in the body and a main port defined in a tip area of the needle. According to one embodiment, the ports allow electromagnetic radiation, such as light and/or infrared radiation, to be carried from a light source to an area to be monitored, and allows electromagnetic radiation to return up the lumen through the main port for evaluation by a sensor or other suitable means to determine a vital. In an alternative embodiment, the main port allows visible light and/or infrared light to be carried to a monitoring area and the side ports allow visible light and/or infrared light to be carried to a sensor.

According to another embodiment of the invention the same fiber optics carry both electromagnetic radiation from the source to the monitoring area and from the monitoring area to a sensor.

According to another embodiment of the invention, the needle has a generally circular cross-section and the body has a series of ports circumscribing the needle along its length proximal the tip end. Alternatively, the needle may have a series of ports traversing a length of the needle and defining a straight line, serpentine configuration, or any other pattern.

According to another embodiment of the invention the needle assembly includes a plurality of barbs (or anchoring means for securing the needle to an area to be monitored) configured for securing the needle assembly in a fixed position in an area to be monitored.

It is another object of the invention to provide methods for using the aforementioned devices to monitor, measure or diagnose a physiological condition or a biological phenomenon. In accordance with this object of the invention, there are provided methods of using these devices in spectrophotometric analysis. Other aspects of the invention include use of these devices in medicine, veterinary medicine, botany, basic science research, and any suitable spectrophotometric method.

The invention as described and claimed herein should become evident to a person of ordinary skill in the art given the following enabling description and drawings. The aspects and features of the invention believed to be novel and other elements characteristic of the invention are set forth with particularity in the appended claims. The drawings are for illustration purposes only and are not drawn to scale unless otherwise indicated. The drawings are not intended to limit the scope of the invention. The following enabling disclosure is directed to one of ordinary skill in the art and presupposes that those aspects of the invention within the ability of the ordinarily skilled artisan are understood and appreciated.

IV. BRIEF DESCRIPTION OF THE DRAWINGS

The following enabling description is provided with reference to the accompanying figures wherein:

FIGS. 1(A) and (B) depict a side cross-sectional view and side view of one embodiment of a fiber optic needle according to the invention, FIG. 2 depicts a side view of an embodiment of a needle body according to the invention, FIG. 3 depicts a side view of another embodiment of a needle body according to the invention, FIG. 4 depicts a front end view of an embodiment of a needle body according to the invention, and FIG. 5 depicts a side view of an embodiment of a barbed needle assembly according to the invention.

While the invention will be described and disclosed in connection with certain preferred embodiments and procedures, it is not intended to limit the invention to those specific embodiments and procedures. Rather it is intended to cover all such alternative embodiments and modifications as fall within the spirit and scope of the invention.

V. DETAILED DESCRIPTION OF THE DRAWINGS

Generally, the present invention relates to devices for monitoring a vital sign or diagnosing a condition in a patient, and in particular, devices using spectrophotometric analysis in doing so. While the present invention is described in connection with a pulse oximeter, it will be readily appreciated by one of ordinary skill in the art that the teachings of the present invention can be applied to a variety of devices in a variety of fields.

For instance, the invention is not limited to spectrophotometric determination of oxyhemoglobin and deoxyhemoglobin. Rather, the present invention should be understood of encompassing spectrophotometric methods of determining other biologically significant analytes, such as cytochrome oxidase, myoglobin, NAD, NADH, NADP, and/or NADPH. For example, not only is the present invention useful for detecting NADP and NADPH because they both absorb light at 260 nm (and can be detected at that wavelength) as a result of the adenine part of the molecule which does not change as a function of the oxidation state; but also the present invention may be particularly suitable for detecting the big increase of absorbance of light at 340 nm which occurs as a result of the transition from oxidized NAD(P)+ to reduced NAD(P)H.

The present invention may be used in connection with other medical and like monitoring of small or difficult to access areas or tissues, analogous uses in veterinary medicine, spectrophotometry in botany, other science research, or any tissue spectrophotometric application in vivo or in vitro for any sized specimens.

Figure 1A:
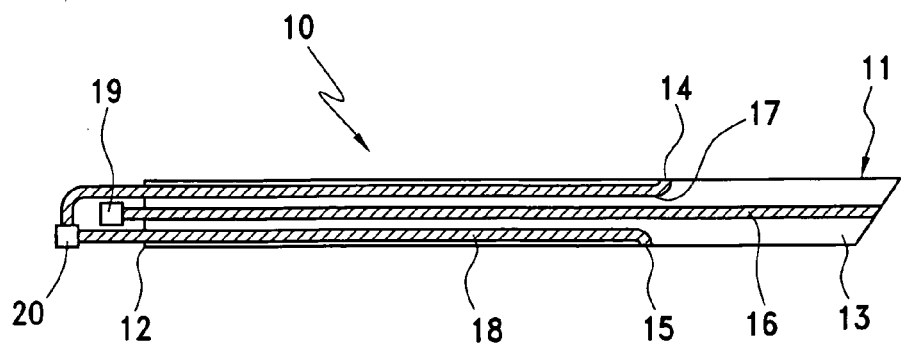

A presently preferred embodiment of the invention is a needle assembly for pulse oximetry. As depicted in FIGS. 1(A) and (B), needle assembly includes a needle body 10 attached to jack 50 via cord 40, light source 19, and light detector 20. As with any needle for delivering a fluid, needle body 10 has a generally uniform and circular cross-section. Needle body 10 is preferably shaped as a long skinny tube having a sharp piercing point on the tip end 11. Between an open back end 12 and the open tip end 11, the body further defines a lumen 13. Also defined by the body 10 are a plurality of ports 14, 15 providing inter-lumenal and extra-lumenal passage. Ports 14, 15 are preferably disposed around the circumference of the body 10 in an area between the back end 12 and the tip end 11.

The assembly includes a plurality of fiber optic members (or means for carrying electromagnetic radiation) 16, 17, 18, preferably in a bundle, positioned within the lumen 13. In the embodiment depicted in FIG. 1 (A), the bundle includes a central fiber optic member 16, first side fiber optic member 17 and second side fiber optic member 18. Central member 16 extends through the lumen 13 to tip end 11. First and second members 17, 18 also extend through lumen 13 to respective side ports 14, 15.

Figure 8:
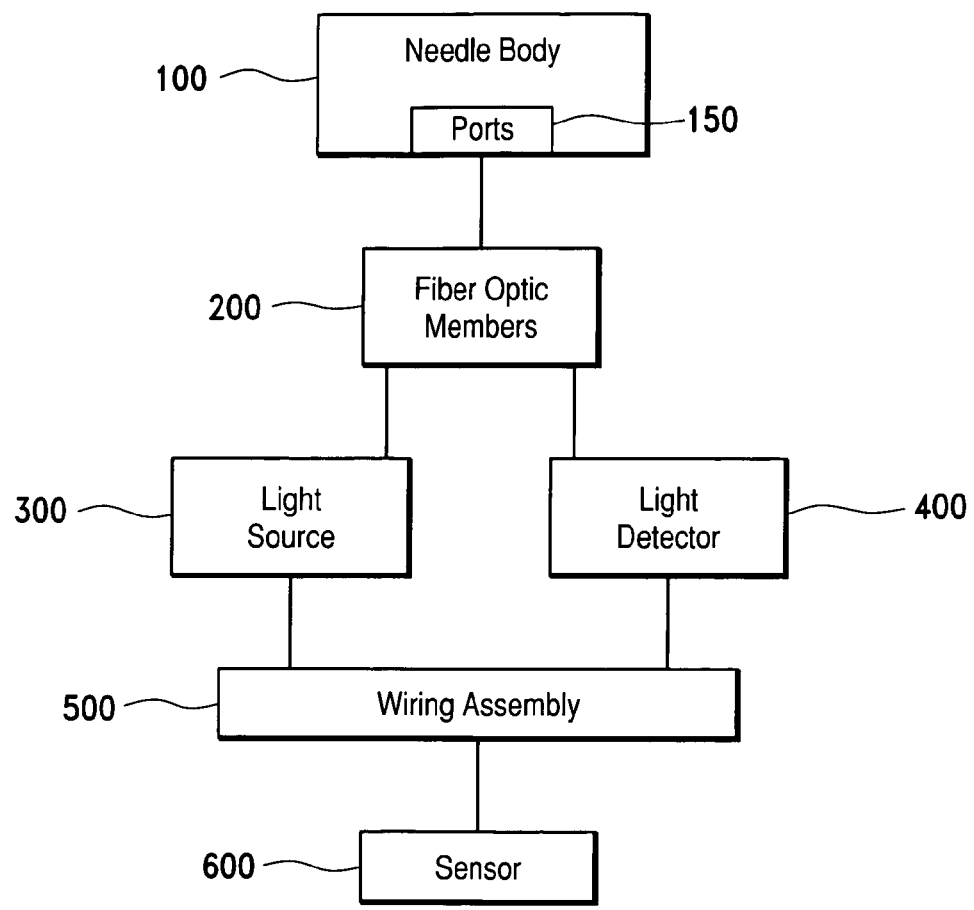
FIG. 8 is a block diagram for a fiber optic needle monitor according to the invention.

Cord 40 connects jack (or connector) 50 to fiber optic members 16, 17, 18 from needle body 10 to jack 50. In a presently preferred embodiment, jack 50 is adapted for coupling with an external sensor (or monitor) 21 as illustrated in FIG. 8. According to this embodiment, sensor 21 may be a spectrophotometer or like device. In a presently preferred embodiment, light source 19, which emits light with wavelengths of 660 nm (red) and 940 nm (near infrared), and light detector 20 communicate with respective fibers of fiber optic members 16, 17, 18. For example light source 19 communicates with fiber optic member 16 and light detector 20 communicates with fiber optic member 17 and port 14 and fiber optic member 18 and port 15.

Figure 1B:
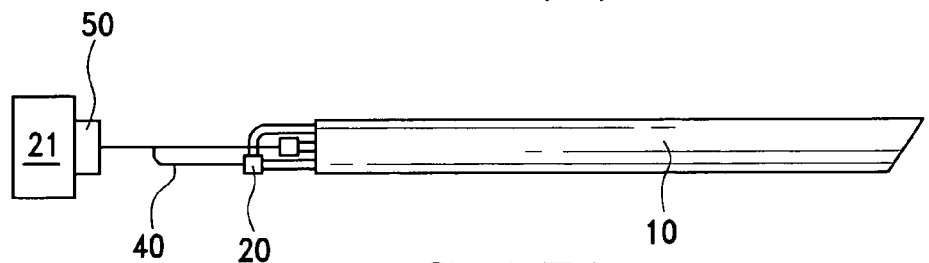

Jack 50 preferably has a standard plug design to interface with a pulse oximetry spectrophotometer, a pulse monitor such as a plethysmograph, or other external sensor 21 or like device. As depicted in FIG. 1, jack 50 may be adapted for coupling to sensor 21 (either indirectly through a cable or directly), which includes light source 19 and light detector 20. According to another embodiment, jack 50 includes a light detector 20 and a light source 19. In yet another alternative embodiment, needle body 10 includes, or is directly coupled to, light source 19 and light detector 20 for example within a housing 30 (illustrated in FIG. 6) attached to back end 12. An alternate embodiment replaces jack 50 with a wireless transmitter to communicate with sensor 21.

As will be appreciated, in embodiments in which light source 19 and/or light detector 20 is included with or near needle body 10, cord 40 preferably comprises an insulated wire for carrying electrical signals from light detector 20 to jack 50 or sensor 21. Alternatively, light source 19 and/or light detector 20 may be housed within jack 50 with cord 40 acting as a conduit for fiber optic members 16, 17, 18.

Light source 19 may be any suitable electromagnetic radiation source, or a plurality of sources, or any like means for providing radiation, preferably light and/or infrared radiation, to a radiation and/or light carrying means, such as central fiber optic member 16. As will be appreciated, light source 19 includes, but is not limited to, any source of radiation used in any spectrophotometric analysis device. In a preferred embodiment, light source 19 emits at least two frequencies of light at, for example, about 660 nm and about 940 nm. The light source 19 preferably is one or more of the following: two light emitters such as light emitting diodes (LED), a bispectral emitter, a dual spectral emitter, a photoemitter, or a semiconductor die. However, any light source that facilitates reflectance pulse oximetry may be employed. Typically, the two emitter arrangement will include a red LED emitting light with a wavelength around or at 660 nm and a near-infrared LED emitting light with a wavelength in the range of 890 to 950 nm and more particularly at about 940 nm. The light source 19 may emit light having a bandwidth, for example, in the range of 20 to 50 nm.

The light detector (or means for detecting electromagnetic radiation) 20 detects light emitted by the light source 19. Electrical signals representing the detected light are transmitted by the light detector 20 to sensor 21. In a preferred embodiment, sensor 21 may be a spectrophotometer, or other similar oximeter device, that discriminates between the relative intensity of these emissions and provides an index as to the degree of oxygen saturation of hemoglobin in blood. Preferably, the light detector 20 may be one of the following: a photoelectric receiver, a photodetector, or a semiconductor die.

Sensor 21 is used generically to indicate any suitable sensor for reading, interpolating, evaluating, sensing or using information or phenomena provided to it for calculating, displaying, reading or manipulating the same to allow a user to discern, calculate, interpolate or establish a vita or a condition, or the absence of a condition. As will be appreciated, sensor 21 includes, but in not limited to, any sensor or sensors adapted to aid in spectrophotometric analysis methods.

Figure 2:
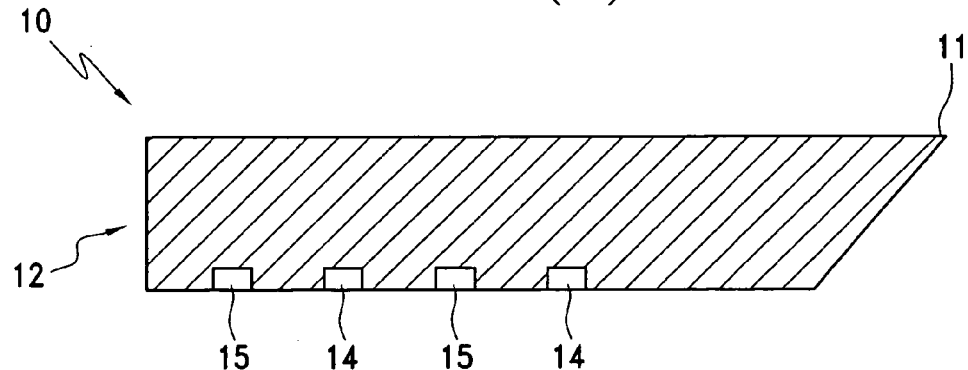

FIG. 2 depicts an alternative embodiment of a needle body 10 according to the invention. In the embodiment depicted in FIG. 2, a plurality of ports 14, 15 are disposed generally equidistantly in a straight line along a length of the body. Accordingly, in this embodiment, ports 14, 15 serve to deliver and carry radiation in the process. Any suitable manner for communicating radiation is contemplated by the invention. For example, ports 14 may communicate with one or more fiber optic members 17 for irradiating the adjacent area and ports 15 may communicate with one or more fiber optic members 18 for receiving radiation and communicating the signal to sensor 20. Alternatively, all of the ports may be couple to a single or multiple fiber optic members and serve dual roles of irradiating and receiving. In addition, alternatively, tip end may be coupled to a central member for radiating and/or receiving radiation, in which case the side ports 14, 15 will preferably perform an opposite role. As exemplified, any combination of irradiating and receiving is considered part of the present invention.

Figure 3:
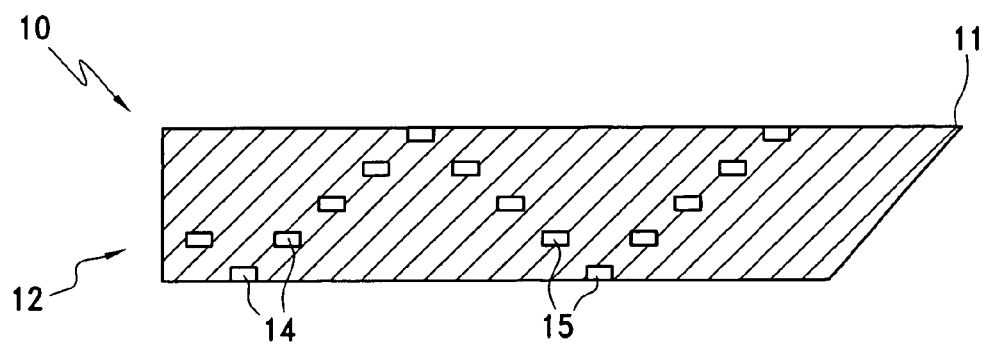

FIG. 3 depicts yet another embodiment of the present invention. According to this embodiment, side ports 14, 15 are disposed in a serpentine configuration along a tip end length of the body 10. As previously discussed, any number of fiber optic members performing single or dual roles is contemplated by the invention, and with or without use of a central fiber optic member. Likewise, as will be appreciated, any pattern or configuration of ports along the body are understood to be contemplated by the present invention.

Figure 4:
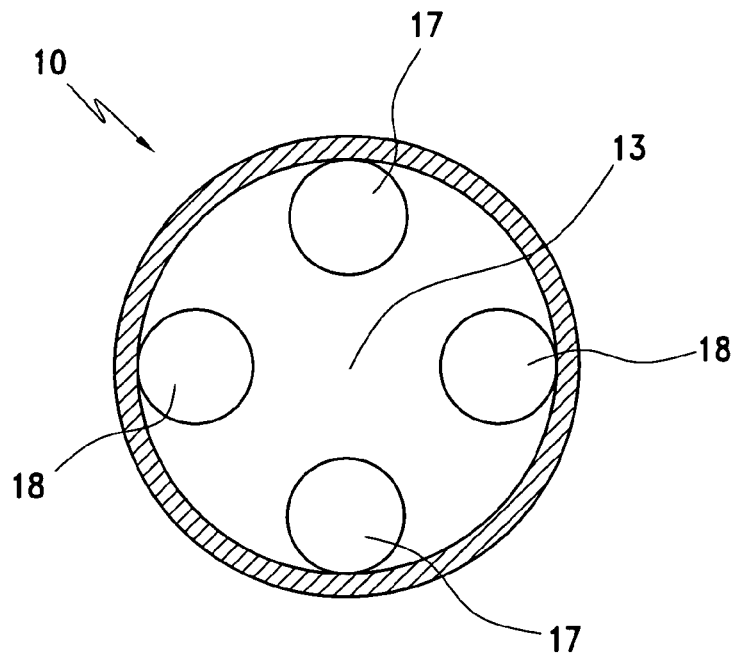

FIG. 4 depicts a four member bundle of fiber optics according to yet another alternative embodiment of the invention. As depicted, each fiber is disposed the length of the needle and responsible for the irradiation and/or receiving for a quarter of the circumference of the area being monitored. In accordance with this embodiment, any combination or computation of irradiating and receiving is contemplated by the embodiment and readily appreciated by one of ordinary skill in the art.

Figure 5:
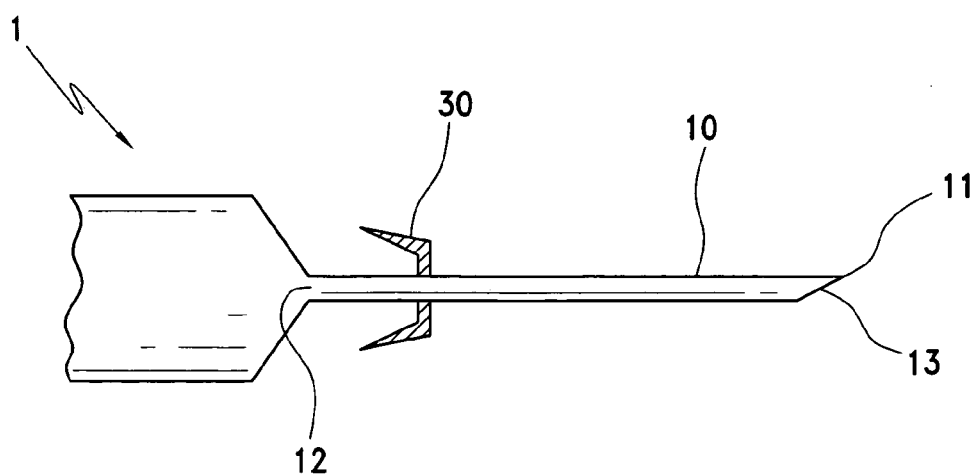

FIG. 5 depicts a front portion of a needle assembly 1 according to the invention. In this embodiment, disposed on or near back end 12 of needle body are barbs 30. Barbs 30 are preferably sized and configured to help anchor or secure needle assembly in place while in use. As will be appreciated, barbs 30 may be advantageous and desirable in, for example, trauma situations when continuous monitoring is desired, yet maintaining intimate contact with a monitoring area may be difficult. Inserting the device subcutaneously or into muscle tissue and anchored into place via barbs is also advantageous in other applications where maintaining device position is desired yet difficult.

Figure 6:
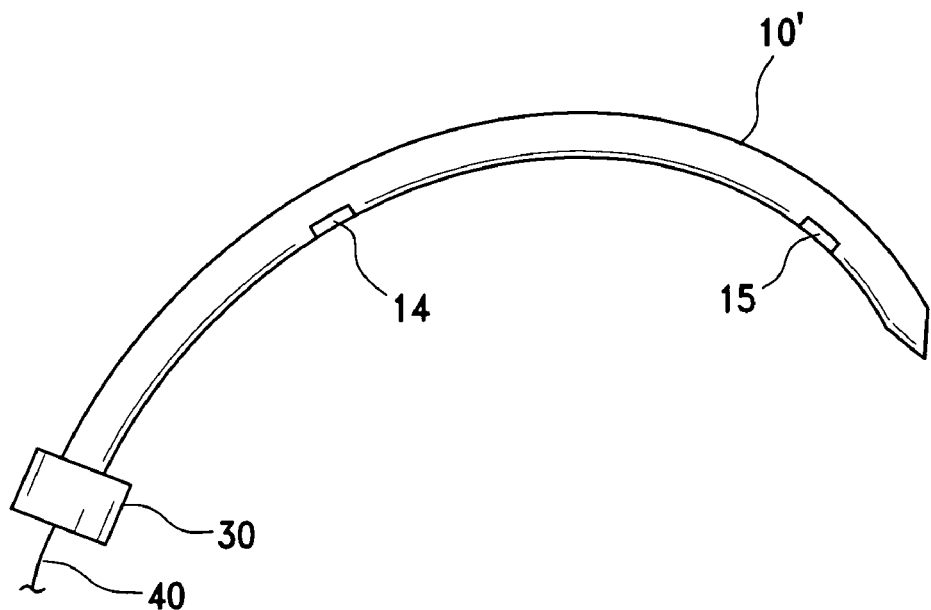
FIG. 6 depicts a side view of a curved needle body embodiment according to the invention.

FIG. 6 depicts another preferred embodiment of the invention. According to this embodiment, needle body 10' has a curved configuration. As will be appreciated, the curved configuration of needle body 10' allows the device to be adapted for not only reflectance spectrophotometry, but also transillumination spectrophotometry. In the case of transillumination spectrophotometry, light is directed from ports 14 disposed on one side of the needle body 10' to ports 15 on the other side of the needle body 10' or vice versa. The amount of light detected at ports 15 may then be communicated to sensor 21. In a preferred embodiment, ports 14 are configured to allow fiber optic members 17 to emit light towards ports 15. According to this embodiment, ports 15 include light detector 20 for detecting light passing from port 14 to port 15. Another embodiment provides ports 14 and 15 paired on both ends of the curve to allow for reflectance spectrophotometry in addition to transilluminated spectrophotometry.

Figure 7:
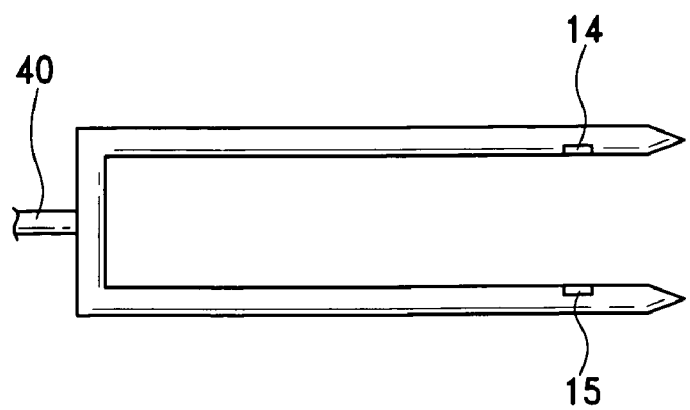
FIG. 7 depicts a side view of a pronged needle body embodiment according to the invention.

FIG. 7 depicts yet another alternative embodiment of the invention. According to this embodiment, needle body 10 has a multi-pronged, or fork, configuration. As will be appreciated, the two-pronged configuration of FIG. 7 allows for one prong to serve as the light emitting side, and the other as the light sensing side, in a transillumination application. Accordingly, ports 14, having light emitting fiber optic members 17, are located on a first prong and directed in the direction of second prong. Second prong includes ports 15 in the path of light from ports 14 for detecting light passing from ports 14, through body tissue, to ports 15. Another embodiment provides ports 14 and 15 paired on both ends of the curve to allow for reflectance spectrophotometry in addition to transilluminated spectrophotometry.

Although FIGS. 6 and 7 were described as including ports, the invention should be understood to include any configuration or material of construction which allows light from one area of the needle body to be emitted and collected, sensed or detected on another area of the needle body.

FIG. 8 depicts a block diagram for a fiber optic needle monitor according to the invention. As depicted, the device includes a needle body 100 in communication with fiber optic members 200. Preferably, the fiber optic members 200 are disposed in the needle body 100 and in communication with one or more ports 150 or areas to allow radiation of tissue adjacent the needle body. The fiber optic members 200 in turn are in communication with a light source 300. The light source 300 may be disposed in any suitable position according to the invention. For example, the light source 300 may be disposed on the back of the needle body itself, or be remote of the needle body, and provide illumination via a fiber optic cord extending from the light source to the fiber optic members disposed in the needle body.

Light detector's 400 role is to receive light which is either backscattered in reflectance spectrophotometry or which passes through tissue in transillumination spectrophotometry. The light detector 400 may be disposed in any suitable position. For example, it may be in direct communication with fiber optic members 200, disposed in the needle or adjacent the back of the needle body 100, or remotely disposed and sense a volume of light through a fiber optic cable or like structure in communication with said needle.

The light source 300 and the light detector 400 communicate with a wiring assembly 500. Wiring assembly 500 is in turn coupled to the sensor 600. However, light detector 400 could be integral with the sensor 600 and thus the signal would travel from wire to the plug and then received by the light detecting portion of the senor.

As previously discussed, sensor 600 may comprise any suitable external device. Alternatively, sensor may be integral with, or immediately adjacent, the needle body. In a presently preferred embodiment, sensor 600 is a spectrophotometer, which is preferably adapted for pulse oximitry.

The devices described herein have numerous uses and applications that will be readily apparent to one of ordinary skill in the art. Specifically for example, needles having fiber optic bundles are small and non-intrusive. Light may be passed through the lumen and reflected back for spectrophotometric analysis from almost any area and for monitoring or analyzing any suitable vita. For example, hand-held Doppler ultrasound is used to monitor surgical flap integrity. Ultrasound is useful only in monitoring larger arteries and gives no information about the circulation at the capillary bed level. The aforementioned devices have the capability to monitor at the capillary bed level. Also, presently monitoring of deep tissues and organs for oxygenation, indocyanin green clearance and other spectrophotometric phenomena is difficult and cumbersome with today's devices. The devices of the present invention allow implantation of the fiber optic sensor precisely and deeply in the area to be monitored.

In addition, as previously indicated pulse oximetry in a trauma situation can be difficult to achieve and maintain. These devices may allow for simple insertion into muscle or subcutaneously and held in place by barbs on the needle to provide continuous readings. Also, surgical flaps and graft often have tenuous blood supplies and it becomes very difficult to monitor them effectively with current techniques. The present invention provides the surgeon with continuous spectrophotometric access to the at risk tissues and allows immediate notice if the tissue becomes compromised. The present invention also provides for use in difficult to monitor patients for pulse oximetry or for spectrophotometric studies of deep tissues and organs.

The present invention is not limited to spectrophotometric analysis of oxyhemoglobin and deoxyhemoglobin, but also encompasses spectrophotometric methods of determining other biologically significant analytes, such as, NAD, NADH, NAP, NAPH, cytochrome oxidase and/or myoglobin.

Moreover, the present invention offers numerous other uses in numerous other fields evident to those of ordinary skill in the art such as veterinary medicine, spectrophotometry in botany, basic science research, any tissue in vivo or in vitro for any specimen of any suitable size for any suitable spectrophotometric analysis.

Those skilled in the art will appreciate that various adaptations and modifications of the above-described preferred embodiments can be configured without departing from the scope and spirit of the invention. Therefore, it is to be understood that, within the scope of the appended claims, the invention may be practiced other than as specifically described herein.

We claim:

1. A monitoring device comprising:
   a needle assembly having a needle body, said needle body having an open back end and a pointed tip end and having a sidewall defining a long-narrow lumen extending between said open back end and said pointed tip end, said sidewall further defining at least three side ports;
   a fiber optic bundle disposed in said lumen and in communication with said ports;
   a radiation delivering fiber optic element disposed in said lumen and in communication with at least one of said ports;
   a radiation source in communication with said radiation delivering fiber optic member for irradiating an area adjacent said at least one of said ports;
   at least one return fiber optic element in communication with the remaining side ports;
   a light detector in communication with said return fiber optic elements for receiving radiation from an irradiated area.

2. The monitoring device of claim 1, further comprising a central port disposed on said pointed tip end, wherein said radiation delivering fiber optic element is in further communication with said central port for irradiating an area adjacent said pointed tip end.

3. The monitoring device of claim 2, wherein said side ports are disposed on said needle body equidistantly from one another.

4. The monitoring device of claim 3, wherein said side ports are disposed generally equidistantly in a straight line along a length of the body.

5. The monitoring device of claim 3, wherein said side ports are disposed around a circumference of said needle body.

6. The monitoring device of claim 3, wherein said side ports are disposed in a serpentine configuration around a length of said needle body.

7. The monitoring device of claim 1, further comprising a sensor for receiving and interpreting information communicated from said light detector.

8. The monitoring device of claim 7, wherein said sensor comprises a photoelectric receiver, a photodetector, a photodiode receiver, or a semiconductor die.

9. The monitoring device of claim 1, wherein said sensor is a spectrophotometer.

10. The monitoring device of claim 9, wherein said device is adapted for spectrophotometric detection of a member selected from the group consisting of oxyhemoglobin, deoxyhemoglobin, NAD, NADH, NADP, NADPH, cytochrome oxidase, and myoglobin.

11. The monitoring device of claim 10, wherein said device is adapted for pulse oximetry.

12. The monitoring device of claim 9, wherein said device is adapted for indocyanine green clearance.

13. The monitoring device of claim 1, wherein said radiation source comprises at least one light emitter, a bispectral emitter, a dual spectral emitter, at least one photoemitter, at least one photodiode, at least one light emitting diode, or a semiconductor die.

14. The monitoring device of claim 1, wherein said pointed tip end is adapted to pierce human tissue.

15. The monitoring device of claim 14, wherein said device includes a barb to anchor said needle in a specimen to be monitored.

16. A monitoring device comprising:
    a needle assembly having a needle body, said needle body having an open back end and a pointed tip end and having a sidewall defining a long-narrow lumen extending between said open back end and said tip, said sidewall further defining at least three side ports;
    means for carrying electromagnetic radiation, said electromagnetic radiation carrying means in communication with said ports;
    means for providing radiation, said radiation means in communication with at least a portion of said electromagnetic radiation carrying means for irradiating an area adjacent said ports; and
    means for detecting electromagnetic radiation, said detecting means in communication with at least a portion of said electromagnetic radiation carrying means for sensing radiation backscattered from an irradiated area.

17. The monitoring device of claim 16, wherein said electromagnetic carrying means comprises at least one fiber optic member.

18. The monitoring device of claim 16, wherein said means for providing radiation comprises at least one light emitter, a bispectral emitter, a dual spectral emitter, at least one photoemitter, at least one photodiode, at least one light emitting diode, or a semiconductor die.

19. The monitoring device of claim 16, wherein said means for detecting electromagnetic radiation comprises a photoelectric receiver, a photodetector, a photodiode receiver, or a semiconductor die.

20. The monitoring device of claim 16, further comprising anchoring means for securing said device to an area to be monitored.

21. The monitoring device of claim 20, wherein said anchoring means comprises at least one barb.

22. A method of detecting or monitoring a physiological condition or biological phenomena with spectrophotometry comprising:
    securing a needle body having a fiber optic bundle disposed therein in an area to be spectrophotometrically analyzed;
    irradiating at least one fiber optic member of said bundle with electromagnetic radiation for delivery to said area through a plurality of ports in said needle body;
    receiving backscattered radiation through additional ports in said needle body and transporting said radiation to a light detector; and
    communicating a signal from said light detector to a sensor configured to decipher a value from said signal.

23. The method of claim 22, wherein said condition or phenomena is oxygen saturation of blood or indocyanine green clearance in said area.

* * * * *